(12) United States Patent
Chow et al.

(10) Patent No.: US 7,323,477 B2
(45) Date of Patent: Jan. 29, 2008

(54) 7-((1H-IMIDAZOL-4-YL)METHYL)-5,6,7,8-TETRAHYDROQUINOLINE

(75) Inventors: Ken Chow, Newport Coast, CA (US); Todd M. Heidelbaugh, Fountain Valley, CA (US); Phong X. Nguyen, Placentia, CA (US); Dale A. Harcourt, Pensacola, FL (US)

(73) Assignee: Allergan, Inc., Irvine, CA (US)

( * ) Notice: Subject to any disclaimer, the term of this patent is extended or adjusted under 35 U.S.C. 154(b) by 46 days.

(21) Appl. No.: 11/345,937

(22) Filed: Feb. 2, 2006

(65) Prior Publication Data

US 2007/0179182 A1 Aug. 2, 2007

(51) Int. Cl.
*A61K 31/4709* (2006.01)
*C07D 215/00* (2006.01)

(52) U.S. Cl. ............... 514/314; 546/112; 546/152; 514/311

(58) Field of Classification Search ........... 546/112, 546/152; 514/311, 314
See application file for complete search history.

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen et al. | |
| 6,465,486 B1 * | 10/2002 | Baxter et al. | 514/311 |
| 7,091,232 B2 * | 8/2006 | Chow et al. | 514/386 |
| 2005/0075366 A1 | 4/2005 | Heidelbaugh et al. | |

FOREIGN PATENT DOCUMENTS

| | | |
|---|---|---|
| WO | WO 92/00073 | 1/1992 |
| WO | WO 01/00586 | 1/2001 |

OTHER PUBLICATIONS

Heidelbaugh et al (2005): STN International HCAPLUS database, Columbus (OH), accession No. 2005: 303397.*
Ruffolo, Jr., "Alpha-Adrenoreceptors: Molecular Biology, Biochemistry and Pharmacology", 1991.
Messier et al, "High Throughput Assays of Cloned Adrenergic, Muscarinic, Neurokinin, and Neurotrophin Receptors in Living Mammalian Cells", 1995, 76, pp. 308-311, Pharmacology & Toxicology.
Conklin et al, Nature, vol. 363, May 20, 1993, pp. 274-276.
Remington's Pharmaceutical Sciences, Mack Publishing Company, 16th Editiion, 1980.

* cited by examiner

*Primary Examiner*—Golam M. M. Shameem
(74) *Attorney, Agent, or Firm*—Brent A. Johnson; Martin A. Voet

(57) ABSTRACT

A compound having a structure

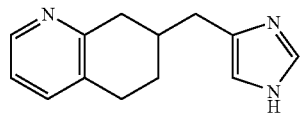

or a pharmaceutically acceptable salt, or a prodrug thereof is disclosed herein. Therapeutic methods, compositions, and medicaments related thereto are also disclosed.

11 Claims, No Drawings

7-((1H-IMIDAZOL-4-YL)METHYL)-5,6,7,8-TETRAHYDROQUINOLINE

BACKGROUND

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction). For a further general background on the $\alpha$-adrenergic receptors, the reader's attention is directed to Robert R. Ruffolo, Jr., $\alpha$-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting $\alpha$-adrenergic receptor affinity is explored.

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha$_2$ adrenergic receptor agonist activity are known analgesics. However, many compounds having such activity do not provide the activity and specificity desirable when treating disorders modulated by alpha$_2$ adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

DESCRIPTION OF THE INVENTION

A compound having a structure

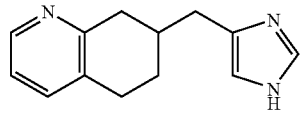

or a pharmaceutically acceptable salt, or a prodrug thereof, is disclosed herein.

A compound which is a (+) enantiomer having a structure

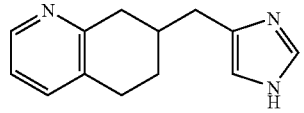

or a pharmaceutically acceptable salt, or a prodrug thereof, is also disclosed herein.

A compound having the name 7-((1H-imidazol-4-yl)methyl)-5,6,7,8-tetrahydroquinoline, or a pharmaceutically acceptable salt, or a prodrug thereof, is also disclosed.

A compound having the name 7-((1H-imidazol-4-yl)methyl)-5,6,7,8-tetrahydroquinoline dihydrochloride is also disclosed.

A compound having the name (+) 7-((1H-imidazol-4-yl)methyl)-5,6,7,8-tetrahydroquinoline, or a pharmaceutically acceptable salt, or a prodrug thereof, is also disclosed.

A compound having the name (+) 7-((1H-imidazol-4-yl)methyl)-5,6,7,8-tetrahydroquinoline dihydrochloride is also disclosed.

A compound which is a (−) enantiomer having a structure

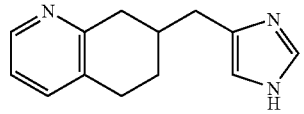

or a pharmaceutically acceptable salt, or a prodrug thereof, is also disclosed herein.

A compound having the name (−) 7-((1H-imidazol-4-yl)methyl)-5,6,7,8-tetrahydroquinoline, or a pharmaceutically acceptable salt, or a prodrug thereof, is also disclosed.

A compound having the name (−) 7-((1H-imidazol-4-yl)methyl)-5,6,7,8-tetrahydroquinoline dihydrochloride is also disclosed.

A "(+)" enantiomer is an enantiomer which, when dissolved in a nonchiral solvent, rotates plane polarized light in the positive or "+" direction. A "(−)" enatiomer rotates plane polarized light in the negative direction when dissolved in a nonchiral solvent. A racemic mixture does not rotate plane polarized light, or is optically inactive.

Also disclosed herein is a racemic mixture of (−) and (+) enantiomers having a structure

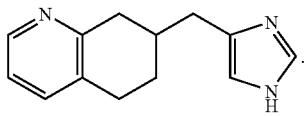

Racemic mixtures of prodrugs are also contemplated. Racemic mixtures of salts of the structure, or racemic mixtures of a combination of salt forms, or racemic mixtures of a combination of one or more salt forms and the neutral form, are also contemplated.

Also disclosed herein is a mixture of the (−) and (+) enantiomers of said structure having (+) optical activity. Mixtures of prodrugs are also contemplated. Mixtures of salts of the structure, or mixtures of a combination of salt forms, or mixtures of a combination of one or more salt forms and the neutral form, are also contemplated.

Also disclosed herein is a composition comprising a compound having said structure, wherein said composition has (+) optical activity. Compositions comprising a prodrug of the compound are also contemplated. Mixtures of salt forms, or mixtures of one or more salt form and the neutral form are also contemplated.

Also disclosed herein is a mixture of the (−) and (+) enantiomers of said structure having (−) optical activity. Mixtures of prodrugs are also contemplated. Mixtures of salts of the structure, or mixtures of a combination of salt forms, or mixtures of a combination of one or more salt forms and the neutral form, are also contemplated.

Also disclosed herein is a composition comprising a compound having said structure, wherein said composition has (−) optical activity. Compositions comprising a prodrug of the compound are also contemplated. Mixtures of salt forms, or mixtures of one or more salt form and the neutral form are also contemplated.

This compound has the tautomeric forms shown below. As used herein, any reference to this compound is intended to include either tautomer and any possible combination of the tautomers.

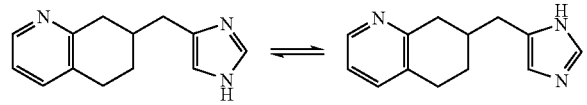

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

The neutral form of a compound is the form wherein the depicted structure has a net neutral formal charge. A salt form of a compound is a form wherein the depicted structure has a net positive or a net negative formal charge and either more or fewer protons (H$^+$) than the depicted structure. The salt form may be associated with a counterion wherein the counterion is closely associated with the charged compound or wherein the counterion is dissociated from the charged compound.

In particular, the dicationic (+2) or diprotonated salts of the compound disclosed herein are contemplated. The dichloride is an example of a dicationic salt. In many circumstances such as in vivo or in a dosage form the compound may be in equilibrium with the neutral form and one or more salt forms. All of these forms are specifically contemplated herein.

Unless a clear intent to the contrary is manifest, a reference to a compound should be construed broadly to include the neutral form, a tautomer of the neutral form, a salt form of the compound, a salt form of a tautomer of the compound, or a mixture of any of the previous forms in any combination.

A "prodrug" is a compound which is converted to a therapeutically active compound after administration, and the term should be interpreted as broadly herein as is generally understood in the art. Generally, but not necessarily, a prodrug is inactive or less active than the therapeutically active compound to which it is converted.

BIOLOGICAL ACTIVITY, MODES OF ADMINISTRATION

TABLE 1

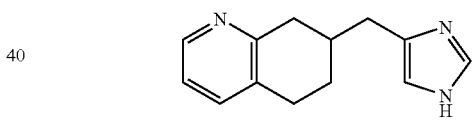

RSAT for adrenergic receptor subtypes: EC50 (nM) and (Relative efficacy)

| Compound | α2A | α2B | α2C | α1A |
|---|---|---|---|---|
| (+) enantiomer | 2.9 nM (0.67 eff) | 0.2 nM (0.98 eff) | 1.1 nM (0.83 eff) | 19.7 nM (0.85 eff) |
| racemic mixture | 3.9 nM (0.72 eff) | 0.1 nM (1.0 eff) | 4.0 nM (1.0 eff) | 38.8 nM (1.43 eff) |
| (−) enantiomer | 58.4 nM (0.33 eff) | 7.0 nM (1.0 eff) | 22.7 nM (0.7 eff) | 806 nM (0.49 eff) |

All compounds have the general structure above.

The compounds disclosed herein are agonists of alpha$_2$ adrenergic receptors. The alpha$_2$ adrenergic activity is demonstrated in an assay titled Receptor Selection and Amplification technology (RSAT) assay, which is described in the publication by Messier et. al., 1995, Pharmacol. Toxicol. 76, pp. 308-311 (incorporated herein by reference) and is also described below. Another reference pertinent to this assay is Conklin et al. (1993) Nature 363:274-6, Receptor Selection and Amplification Technology (RSAT) assay, also incorporated herein by reference.

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha$_2$ receptors, which normally couple to G$_i$, activate the RSAT response when coexpressed with a hybrid Gq protein that has a G$_i$ receptor recognition domain, called G$_{q/i5}$.

NIH-3T3 cells are plated at a density of 2×10$^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, the chemical structure of which is shown below, is used as the standard agonist for the alpha$_{2A}$, alpha$_{2B}$ and alpha$_{2C}$ receptors.

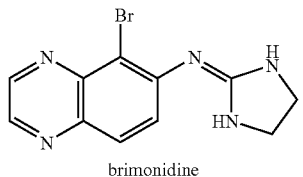

brimonidine

The results of the RSAT assay of the compounds disclosed herein are shown in Table 1 above together with the chemical formulas of these exemplary compounds. NA stands for "not active" at concentrations less than 10 micromolar.

Efficacy of these compounds in reducing intraocular pressure is shown in Table 2.

TABLE 2

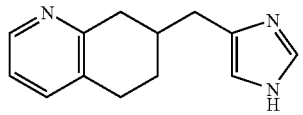

Effects of compounds on IOP as measured in the telemetrized primate model.

| Compound | Dose (%) | % IOP decrease from baseline in the hypertensive eye |
|---|---|---|
| (+) enantiomer | 0.15 | 30 |
| racemic mixture | 0.30 | 30 |
| (−) enantiomer | 0.30 | 0 |

All compounds have the general structure above.

Conventional Intraocular Pressure (IOP) Model.

Cynomolgus (macaca fascicularis) monkeys weighing 3-5 kg with unilateral ocular hypertension in the right eye (OD) are used. Sustained elevated IOP is created by circumferential argon laser photocoagulation (Zeiss Visulas 532) of the mid-trabecular meshwork according to the method of Gaasterland and Kupfer (5). IOPs are assessed at T=−0.1, 0, 1, 2, 4, and 6, hours with an optional reading at 24 hours using an applanation pneumatonometer (Model 30 Classic, mentor Co). A drop of proparacaine (Allergan, Inc.) is instilled into the eyes just prior to IOP measurements. Monkeys are chaired and conditioned for tonometry for months before initiation of the study. Results are averaged from the 2 hr to the 6 hr time points (averages for each animal are calculated and the group mean determined) in an effort to simplify and standardize the data and include a comparison of sustained responses. Depending on the design of the study, either a paired or unpaired Student's t test is done. P<0.05 is considered significant.

Telemetry IOP model. Cynomolgus monkeys (3-5 kg) are made unilaterally ocular hypertensive by argon laser as noted above. The telemetry implant procedure is performed following elevation of IOP. Briefly, the scalp is prepared for aseptic surgery, followed by a 4 cm incision and tissue blunt-dissection to form a pocket in the underlying fascia to contain the pressure transducer. The catheter from the transducer is then guided subcutaneously to the orbit, and inserted into the vitreous cavity of the glaucoma eye through a small opening in the pars plana which is sutured closed and fixed with tissue adhesive. Receivers are placed into the animal cages and connected to a computer running Dataquest software for data capture. Animals are housed in a 12 hours light, 12 hours dark cycle: 6:00 AM ON, 6:00 PM OFF. Animals are used in drug studies following recovery from the surgical procedure which takes 2 weeks to 1 month. Dosing is done by transferring animals to restraining chairs. Animals are dosed without the aid of a sedative. Animals are normally dosed from 9:00-9:30 am unless noted otherwise. Following dosing, animals are returned to cages for continued data acquisition. Each data point is the running average of signals generated for a given hour. Data are acquired for 30 secs @ 1000 Hz every 5 mins for each animal. The 5 minute data are then averaged for each hour. Results are averaged from 12:30 pm to 6:30 pm to assess a sustained diurnal effect, and from 7:30 pm to 5:30 am to assess a sustained nocturnal effect. This analysis represents an effort to simplify and standardize the data and include a comparison of sustained responses. Statistical comparisons are made between baseline and drug days @ each time point using a paired Student's t test. P values of <0.05 are considered statistical significant Diseases that may be treated with compounds disclosed herein include, but are not limited to neurodegenerative aspects of the following conditions:

MACULOPATHIES/RETINAL DEGENERATION Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration, UVEITIS/RETINITIS/CHOROIDITIS/OTHER INFLAMMATORY DISEASES Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigement Epitheliitis, Acute Macular Neuroretinopathy VASUCLAR DISEASES/EXUDATIVE DISEASES Diabetic retinopathy, Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease TRAUMATIC/SURGICAL/ENVIRONMENTAL Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy PROLIFERATIVE DISORDERS Proliferative Vitreal Retinopathy and Epiretinal Membranes INFECTIOUS DISORDERS Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis GENETIC DISORDERS Retinitis Pigmentosa, Systemic Disorders with Accosiated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum RETINAL TEARS/HOLES Retinal Detachment, Macular Hole, Giant Retinal Tear TUMORS Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

Generally speaking alpha$_2$ agonists, can alleviate sympathetically-sensitized conditions that are typically associated with periods of stress. These include neurological conditions of: 1) increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8). behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

Alpha$_2$ agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

Thus, the compounds disclosed herein are useful for treating neurological conditions of conditions and diseases which are responsive to treatment by alpha$_2$ adrenergic agonists. Such conditions and diseases include, but are not limited to, pain including chronic pain (which may be, without limitation visceral, inflammatory, referred or neuropathic in origin) neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy. In addition, the compounds disclosed herein are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel syndrome (IBS), functional dyspepsia and ulcerative colitis. The activity of the alpha$_{2B/2C}$ specific or selective compounds disclosed herein is highly advantageous because the administration of these compounds to mammals does not result in sedation or in significant cardivascular effects (such as changes in blood pressure or heart rate).

The compounds disclosed herein may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

Also disclosed herein are therapeutic compositions comprising the compounds disclosed herein and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as a excipient or vehicle for the active compound. The formulations may also include wetting agents, emulsifying agents, preserving agents, sweetening agents, and/or flavoring agents. If used in an ophthalmic or infusion format, the formulation will usually contain one or more salts to influence the osmotic pressure of the formulation.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |

-continued

| Ingredient | Amount (% w/v) |
| --- | --- |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenerpic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

Other embodiments are methods for the treatment of pain, particularly chronic pain, through the administration of one or more compounds disclosed herein or pharmaceutically acceptable salts thereof to a mammal in need thereof. As indicated above, the compound will usually be formulated in a form consistent with the desired mode of delivery.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (Aβ and A fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by Aβ afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

SPECIFIC EMBODIMENTS, EXPERIMENTAL

Procedure for the preparation of 7-(1H-imidazol-4-ylmethyl)-5,6,7,8-tetrahydro-quinoline dihydrochloride and the (+) enantiomer, Compound 2

Reagents: 5,6,7,8-tetrahydroquinoline was purchased from TCI. All reagents were commercially available from Aldrich, and no further purification was done.

A solution of 5,6,7,8-tetrahydroquinoline (18.2 g, 137 mmol), benzaldehyde (17.67 g, 166.0 mmol), and acetic anhydride (24.5 mL, 254 mmol) was heated under a nitrogen environment at 165° C. for 16 hours. The reaction mixture was cooled to room temperature. Crushed ice was added,

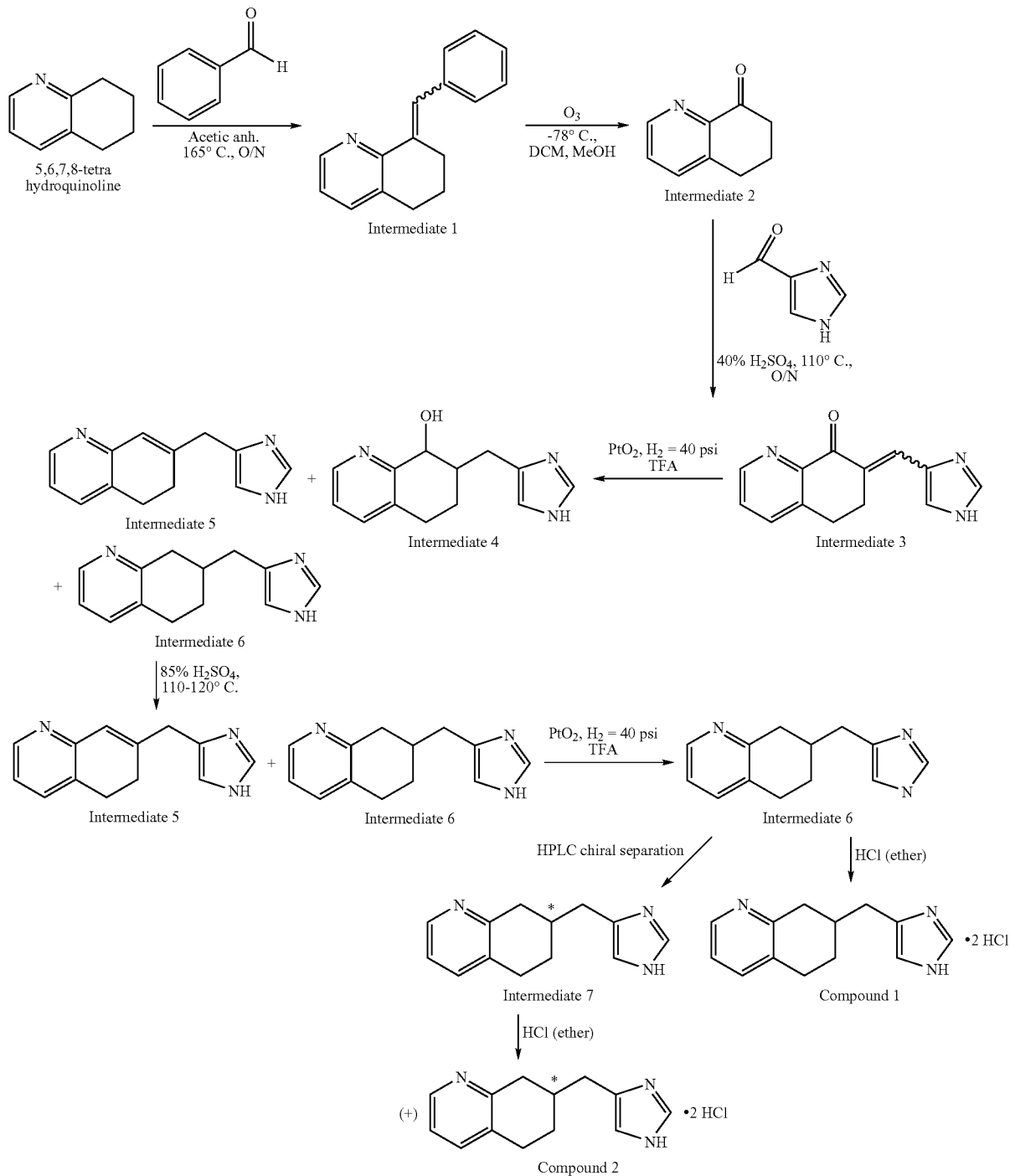

and the mixture was slowly basified with NaOH (solid then 2 N NaOH) to pH around 7. The aqueous layer was extracted with hexane/ethyl acetate (1:1 solution) 3 times. The pooled organic layers were dried over magnesium sulfate. The mixture was filtered, and the solvents were removed under vacuum to give 8-benzylidene-5,6,7,8-tetrahydro-quinoline (Intermediate 1) as a brown solid. A solution of Intermediate 1 in dichoromethane (100 mL) and methanol (500 mL) was cooled to −78° C. (dry ice/acetone bath), and charged with ozone/oxygen (3 psi, 1.5 ampere). The dark brown solution turned yellow after several hours. When Intermediate 1 was consumed (TLC), ozone/oxygen flow was stopped. The reaction mixture was purged with nitrogen for 10 minutes. Methyl sulfide (6 mL) was added, and the mixture was stirred for 30 minutes at room temperature. The solvents were removed under vacuum. The residue was dissolved in 1 N HCl (500 mL), and washed with diethyl ether (4×150 mL). The aqueous layer was basified to pH ~7 with NaOH (s), and extracted with ethyl acetate (2×200 mL). The pooled ethyl acetate layers were dried over magnesium sulfate. The mixture was filtered and the solvent was removed under vacuum. The residue was purified by chromatography on silica gel with 90% EtOAc: hexane to give a clean product. The aqueous layer was extracted with chloroform/isopropanol (3:1) several times. The pooled chloroform/isopropanol layers were dried over magnesium sulfate. The mixture was filtered and the solvents were removed under vacuum to give 6,7-dihydro-5H-quinolin-8-one (Intermediate 2), 17.89 g (122.0 mmol, 89% over 2 steps).

A solution of Intermediate 2 (17.89 g, 122.0 mmol) and imidazole-4-carboxaldehyde (14.35 g, 146.0 mmol) in 40% sulfuric acid (100 mL) was heated at 110° C. for 16 hours. The reaction was cooled to room temperature. Crushed ice was added and the mixture was stirred vigorously, while NaOH(s) was added carefully. At pH ~4, one isomeric product precipitated from solution. The mixture was stirred for 30 minutes, and filtered to isolate the product as a yellow solid. The filtrate was basified with NaOH (2N) to pH ~7 and a brown solid precipitated. The mixture was filtered to isolate the other isomeric product. The total weight of crude 7-(1H-imidazol-4-ylmethylene)-6,7-dihydro-5H-quinolin-8-one (Intermediate 3) was 32.50 grams.

A mixture of Intermediate 3 (11.21 g, 49.80 mmol) and platinum oxide (1.10 gram, 4.84 mmol) in TFA (50 ml) was hydrogenated at 40 psi. at room temperature. After one hour, mass spectrometry analysis confirmed the reduction of Intermediate 3, and the formation of 7-(1H-imidazol-4-ylmethyl)-5,6,7,8-tetrahydro-quinolin-8-ol (Intermediate 4, major), 7-(1H-imidazol-4-ylmethyl)-5,6-dihydro-quinoline (Intermediate 5, minor) and 7-(1H-imidazol-4-ylmethyl)-5,6,7,8-tetrahydro-quinoline (Intermediate 6, minor). The mixture was filtered through a bed of Celite®, and the Celite® bed was washed with methanol. The solvents were evaporated under vacuum. The residue was dried under high vacuum for 16 hours, and heated at 110° C. in 85% sulfuric acid (aq, 20 mL). After 3 hours, mass spectrometry analysis showed Intermediate 4 remained. Sulfuric acid (10 mL of 85%) was added and the reaction mixture was heated at 115° C. for 3 hours. Another aliquot of 85% sulfuric acid (10 mL) was added and the reaction mixture was heated at 120° C. for 5 hours. The reaction mixture was cooled to room temperature. Crushed ice was added and the mixture was basified with NaOH (s) to pH ~7. The aqueous layer was extracted with chloroform/isopropanol (3:1) 4 times. The pooled organic layers were dried over magnesium sulfate, filtered, and the solvents were removed under vacuum. Proton NMR identified products to be a mixture of Intermediate 5 (70%), and Intermediate 6 (30%). Intermediate 5 and Intermediate 6 and platinum oxide (1.10 g, 4.84 mmol) in trifluoroacetic acid were hydrogenated at 40 psi for one hour at room temperature. The mixture was filtered through a bed of Celite® and washed through with methanol. The solvents were evaporated under vacuum. The residue was basified with NaOH (2 N) to pH ~7, and extracted with chloroform/isopropanol (3:1) three times. The pooled organic layers were dried over magnesium sulfate. The mixture was filtered and the solvents were removed under vacuum. The residue was purified by chromatography on silica gel with 5% ammonia methanol 95% dichloromethane to give Intermediate 6 as oil (3.20 g, 15.0 mmol, 30% yield from Intermediate 3).

A solution of Intermediate 6 (0.189 g, 0.887 mmol) in dichloromethane was treated with HCl in ether (1.80 mL, 1M, 1.80 mmol) at room temperature. White precipitates formed. Methanol was added to homogenize the mixture. The resulting solution was stirred for 15 minutes and the solvents were removed under vacuum. The residue was diluted with dichloromethane/ether (3-4 mL) and evaporated under vacuum to give a white solid. The mixture was dried under high vacuum overnight. 7-(1H-Imidazol-4-ylmethyl)-5,6,7,8-tetrahydro-quinoline dihydrochloride (Compound 1) was isolated as a white solid (0.161 g, 0.563 mmol, 63% yield).

$^1$H NMR (300 MHz, CD$_3$OD): δ 8.89 (s, 1H), 8.57 (d, J=5.7 Hz, 1H), 8.35 (d, J=7.8 Hz, 1H), 7.82 (dd, J=7.5, 5.7 Hz; 1H), 7.48 (s, 1H), 3.27-2.84 (series of m, 6H), 2.45-2.30 (m, 1H), 2.17-2.07 (m, 1H), 1.69-1.56 (m, 1H).

Compound 1 was separated by chiral HPLC: CHIRALCEL® OD with 80% hexane and 20% IPA at room temperature. The (+)-enantiomer (Intermediate 7) corresponding to the second eluting peak was converted to the dihydrochloride salt by the procedure described above to give (+)-7-(1H-imidazol-4-ylmethyl)-5,6,7,8-tetrahydroquinoline dihydrochloride (Compound 2), $[\alpha]_D^{20}$+79.2° (c=1.16 in methanol).

What is claimed is:

1. A compound having a structure

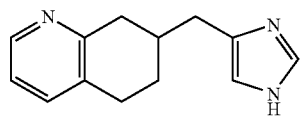

or a pharmaceutically acceptable salt, or a prodrug thereof.

2. The compound of claim 1 which is a (+) enantiomer.

3. The compound of claim 2 which is the (+) enantiomer and is a pharmaceutically acceptable salt.

4. The compound of claim 3 which is a dicationic salt.

5. The compound of claim 4 which is a dihydrochloride salt.

6. The compound of claim 1 which is a (−) enantiomer.

7. The compound of claim 2 which is

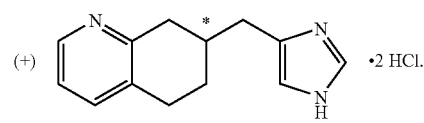

8. A composition comprising a compound having a structure
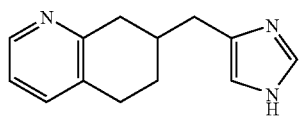
wherein said compound may be in neutral form, a salt form, or a combination thereof.
9. The composition of claim 8 which has (+) optical activity.
10. The composition of claim 8 which has (−) optical activity.
11. The composition of claim 8 which is optically inactive.
* * * * *